(12) United States Patent
Ikemoto et al.

(10) Patent No.: US 10,040,760 B2
(45) Date of Patent: Aug. 7, 2018

(54) PYRROLIDINE COMPOUND

(71) Applicant: SUMITOMO CHEMICAL COMPANY, LIMITED, Tokyo (JP)

(72) Inventors: Tetsuya Ikemoto, Osaka (JP); Leopold Mpaka Lutete, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/566,847

(22) PCT Filed: Apr. 8, 2016

(86) PCT No.: PCT/JP2016/061479
§ 371 (c)(1),
(2) Date: Oct. 16, 2017

(87) PCT Pub. No.: WO2016/171000
PCT Pub. Date: Oct. 27, 2016

(65) Prior Publication Data
US 2018/0127364 A1    May 10, 2018

(30) Foreign Application Priority Data
Apr. 21, 2015   (JP) .................... 2015-086929

(51) Int. Cl.
| C07D 207/08 | (2006.01) |
| C07D 207/09 | (2006.01) |
| C07C 67/343 | (2006.01) |
| C07C 69/716 | (2006.01) |
| B01J 31/02  | (2006.01) |
| C07C 67/317 | (2006.01) |

(52) U.S. Cl.
CPC ........ C07D 207/09 (2013.01); B01J 31/0271 (2013.01); C07C 67/317 (2013.01); C07C 67/343 (2013.01); C07C 69/716 (2013.01); C07D 207/08 (2013.01)

(58) Field of Classification Search
CPC .. C07D 207/08; C07D 207/09; C07C 67/343; C07C 69/716
See application file for complete search history.

(56) References Cited

U.S. PATENT DOCUMENTS

2013/0137880 A1   5/2013   Hayashi

FOREIGN PATENT DOCUMENTS

| EP | 2 883 858 | 6/2015 |
| JP | 2011-251924 | 12/2011 |

OTHER PUBLICATIONS

C. Sparr, et al., "A Concise Synthesis of (S)-2-(Fluorodiphenylmethyl)pyrrolidine: A Novel Organocatalyst for the Stereoselective Epoxidation of α,β-Unsaturated Aldehydes," Synthesis (2010), No. 8, pp. 1394-1397.
T. Urushima, et al., "Polymeric Ethyl Glyoxylate in an Asymmetric Aldol Reaction Catalyzed by Diarylprolinol," Organic Letters (2010), v. 12, No. 13, pp. 2966-2969.
U. Jahn, et al., "Triarylaminium Salt Induced Oxidative Cyclization of Tertiary Amines. Convenient Access to 2-Substituted Pyrrolidinium Salts," Organic Letters (1999), v. 1, No. 6, pp. 849-852.

(Continued)

Primary Examiner — Laura L Stockton
(74) Attorney, Agent, or Firm — Foley & Lardner LLP

(57) ABSTRACT

Compound (1) is useful as a catalyst since compound (III) can be obtained by reacting compound (I) with compound (II) in the presence of compound (I).

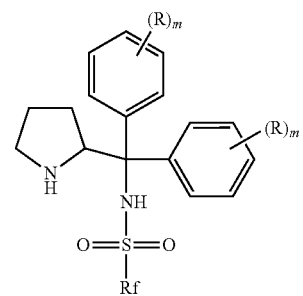

(1)

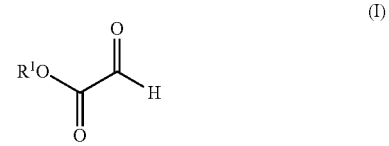

(I)

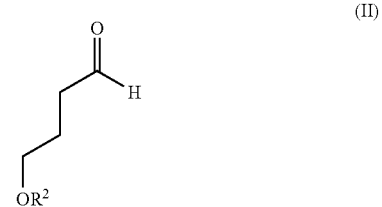

(II)

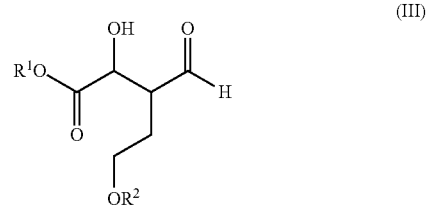

(III)

In particular, an optically active substance of compound (III) can be produced by using compound (I) which is optically active.

8 Claims, No Drawings

(56) References Cited

OTHER PUBLICATIONS

International Search Report issued in International Patent Application No. PCT/JP2016/061479 dated Jun. 14, 2016.
Notification of Transmittal of the English Translation of the International Preliminary Report on Patentability (Chapter I) from International Application No. PCT/JP2016/061479 dated Nov. 2, 2017.

PYRROLIDINE COMPOUND

The present application claims priority under 35 USC 371 to International Patent Application number PCT/JP2016/061479, filed Apr. 8, 2016, which claims priority to Japanese Patent Application No. JP 2015-086929, filed Apr. 21, 2015.

TECHNICAL FIELD

The present invention relates to a pyrrolidine compound, a method for producing the pyrrolidine compound, and use of the pyrrolidine compound as a catalyst.

BACKGROUND ART

3-Formyl-2-hydroxypropanoic acid compounds are useful as an active ingredient for medicines, agrochemicals and the like or as an intermediate in the production of medicines, agrochemicals and the like. In particular, an optically active form of the compound is useful as an intermediate in the production of vitamins including pantothenic acid.

The method for producing an optically active form of a 3-formyl-2-hydroxypropanoic acid compound is disclosed in EP 2883858A, US 2013/137880 and Organic Letters, 2010, Vol. 12, No. 13, pp 2966-2969, in which a glyoxylic acid compound and an aldehyde are subjected to an asymmetric aldol reaction in the presence of, for example, a catalyst shown below.

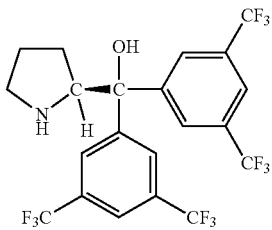 [SMILES: OC(c1cc(C(F)(F)F)cc(C(F)(F)F)c1)(c1cc(C(F)(F)F)cc(C(F)(F)F)c1)[C@@H]1CCCN1]

SUMMARY OF THE INVENTION

The present invention provides: a novel catalyst; a method for producing the catalyst; and a method for producing a 3-formyl-2-hydroxypropanoic acid compound using the catalyst.

Namely, the present invention provides:
1. A compound represented by formula (1) (hereinafter referred to as "compound (1)"):

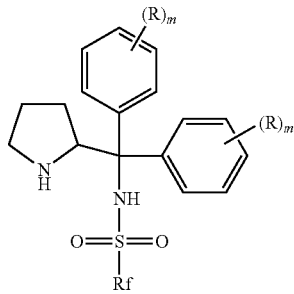

(wherein Rf represents a $C_1$-$C_8$ perfluoroalkyl group; R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom, and m represents an integer of 0 to 3, wherein multiple Rs may be the same as or different from each other when m is 2 or 3);

2. A method for producing compound (1), comprising the steps of:

producing a compound represented by formula (3) (hereinafter referred to as "compound (3)"):

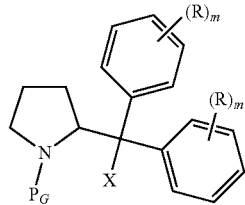

(wherein $P_G$ represents a protecting group for an amino group, X represents a leaving group; and R and m are as defined above) from a compound represented by formula (2) (hereinafter referred to as "compound (2)"):

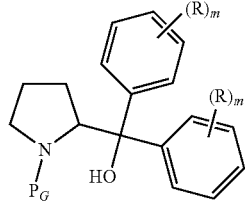

(wherein $P_G$, R and m are as defined above);

producing a compound represented by formula (4) (hereinafter referred to as "compound (4)"):

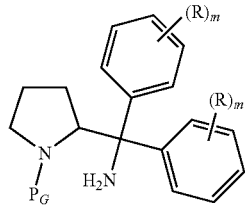

(wherein $P_G$, R and m are as defined above) or a salt thereof from compound (3) and ammonia;

producing a compound represented by formula (5) (hereinafter referred to as "compound (5)"):

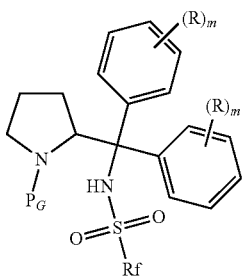

(5)

(wherein Rf, $P_G$, R and m are as defined above) from the compound (4) or a salt thereof; and
deprotecting compound (5);

3. A method for producing compound (1), comprising the steps of: producing compound (3) from compound (2); producing compound (5) from compound (3) and a $C_1$-$C_8$ perfluoroalkanesulfonamide or a salt thereof; and deprotecting compound (5); and 4. A method for producing a compound represented by formula (III) (hereinafter referred to as "compound (III)"):

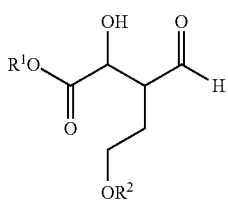

(III)

(wherein $R^1$ represents a protecting group for a carboxyl group and $R^2$ represents a protecting group for a hydroxyl group) comprising the step of:
reacting a compound represented by formula (I) (hereinafter referred to as a "compound (I)"):

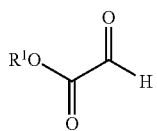

(I)

(wherein $R^1$ is as defined above)
or a polymer thereof with a compound represented by formula (II) (hereinafter referred to as "compound (II)"):

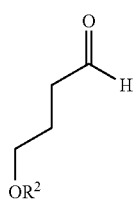

(II)

(wherein $R^2$ is as defined above)
in the presence of compound (1).

MODE FOR CARRYING OUT THE INVENTION

In the description, the halogen atom refers to a fluorine atom, a chlorine atom, a bromine atom or an iodine atom.

The $C_1$-$C_8$ perfluoroalkyl group represented by Rf refers to a group in which all of hydrogen atoms in a $C_1$-$C_8$ alkyl group are substituted by fluorine atoms, and specific examples thereof include a trifluoromethyl group, a pentafluoroethyl group and a nonafluorobutyl group. In the present invention, Rf is preferably a $C_1$-$C_4$ perfluoroalkyl group, more preferably a trifluoromethyl group.

The $C_1$-$C_{12}$ alkyl group represented by R refers to a linear or branched alkyl group having 1 to 12 carbon atoms, and specific examples thereof include a methyl group, an ethyl group, a propyl group, an isopropyl group, a butyl group, an isobutyl group, a sec-butyl group, a tert-butyl group, a neopentyl group, a 1-ethylpropyl group, a hexyl group, a 2,2-dimethylbutyl group, a heptyl group, an octyl group, a decyl group and a dodecyl group. Among these groups, a $C_1$-$C_8$ alkyl group is preferred, and a $C_1$-$C_4$ alkyl group is particularly preferred.

The $C_1$-$C_{12}$ alkoxy group represented by R refers to a linear or branched alkoxy group having 1 to 12 carbon atoms, and specific examples thereof include a methoxy group, an ethoxy group, a propoxy group, an isopropoxy group, a butoxy group, a tert-butoxy group, a neopentyloxy group, a hexyloxy group, an octyloxy group, a decyloxy group and a dodecyloxy group. Among these groups, a $C_1$-$C_6$ alkoxy group is preferred, and a $C_1$-$C_4$ alkoxy group is particularly preferred.

The $C_2$-$C_{13}$ alkoxycarbonyl group represented by R refers to a group in which a $C_1$-$C_{12}$ alkoxy group is bound to —C(=O)—, and specific examples thereof include a methoxycarbonyl group, an ethoxycarbonyl group, a propoxycarbonyl group, an isopropoxycarbonyl group, a butoxycarbonyl group, a tert-butoxycarbonyl group, a neopentyloxycarbonyl group, a hexyloxycarbonyl group, an octyloxycarbonyl group, a decyloxycarbonyl group and a dodecyloxycarbonyl group. Among these groups, a $C_2$-$C_7$ alkoxycarbonyl group is preferred.

The $C_1$-$C_{12}$ fluorinated alkyl group represented by R refers to a $C_1$-$C_{12}$ alkyl group having a fluorine atom, and specific examples thereof include a fluoromethyl group, a difluoromethyl group, a trifluoromethyl group, a 2-fluoroethyl group, a 2,2-difluoroethyl group, a 3-fluoropropyl group, a 4-fluorobutyl group, an 8-fluorooctyl group and a 12-fluorododecyl group.

In compound (1), R is preferably a $C_1$-$C_{12}$ alkyl group or a $C_1$-$C_{12}$ fluorinated alkyl group, more preferably a $C_1$-$C_4$ alkyl group or a $C_1$-$C_4$ fluorinated alkyl group. Particularly preferred specific examples of R include a methyl group, an ethyl group and a trifluoromethyl group. m is preferably an integer of 0 to 2, more preferably 0.

Compound (1) has an asymmetric carbon atom, and therefore includes a compound represented by formula (1S) that is in an S steric configuration (hereinafter referred to as "compound (1S)") and a compound represented by formula (1R) that is in an R steric configuration (hereinafter referred to as "compound (1R)").

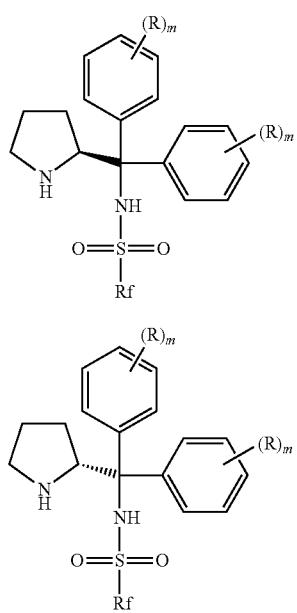

Compound (1) can be used as a catalyst for the below-mentioned aldol reaction.

An optically active form of compound (1) can be used as an asymmetric catalyst. In this case, because the enantiomeric excess of the optically active form of compound (1) affects the enantiomeric excess of a product, compound (1) to be used in the asymmetric aldol reaction preferably has an enantiomeric excess of 90 ee % or more, more preferably 95 ee % or more.

Compound (1) can be synthesized by, for example, the following method.

Specific examples of the protecting group for an amino group (hereinafter referred to as "amino-group-protecting group") represented by $P_G$ include a $C_1$-$C_6$ alkyl group (e.g., a methyl group, an ethyl group, a propyl group, an isopropyl group, a butyl group, an isobutyl group, a sec-butyl group, a tert-butyl group, a neopentyl group, a 1-ethylpropyl group, a hexyl group, a 2,2-dimethylbutyl group, a 2-ethylbutyl group), a $C_2$-$C_6$ alkenyl group (e.g., an ethenyl group, a 1-propenyl group, a 2-propenyl group, a 2-methyl-1-propenyl group, a 1-butenyl group, a 3-methyl-2-butenyl group, a 2-pentenyl group, a 4-methyl-3-pentenyl group, a 1-hexenyl group, a 3-hexenyl group), a $C_6$-$C_{10}$ aryl group (e.g., a phenyl group, a 1-naphthyl group, a 2-naphthyl group), a $C_7$-$C_{14}$ aralkyl group (e.g., a benzyl group, a 1-phenylethyl group, a 2-phenylethyl group, a (naphthyl-1-yl)methyl group, a (naphthyl-2-yl)methyl group, a 1-(naphthyl-1-yl)ethyl group, a 1-(naphthyl-2-yl)ethyl group, a 2-(naphthyl-1-yl)ethyl group, a 2-(naphthyl-2-yl)ethyl group), a formyl group, a $C_2$-$C_7$ alkylcarbonyl group (e.g., an acetyl group, a propanoyl group, a butanoyl group, a 2-methylpropanoyl group, a pentanoyl group, a hexanoyl group, a heptanoyl group), a $C_2$-$C_7$ alkoxycarbonyl group (e.g., a methoxycarbonyl group, an ethoxycarbonyl group, a propoxycarbonyl group, an isopropoxycarbonyl group, a butoxycarbonyl group, a tert-butoxycarbonyl group, a neopentyloxycarbonyl group, a hexyloxycarbonyl group), a $C_3$-$C_7$ alkenyloxycarbonyl group (e.g., an ethenyloxycarbonyl group, a 1-propenyloxycarbonyl group, a 2-propenyloxycarbonyl group, a 2-methyl-1-propenyloxycarbonyl group, a 1-butenyloxycarbonyl group, a 3-methyl-2-butenyloxycarbonyl group, a 2-pentenyloxycarbonyl group, a 4-methyl-3-pentenyloxycarbonyl group, a 1-hexenyloxycarbonyl group, a 3-hexenyloxycarbonyl group), a $C_7$-$C_{11}$ arylcarbonyl group (e.g., a benzoyl group, a 1-naphthoyl group, a 2-naphthoyl group), a $C_8$-$C_{15}$ aralkylcarbonyl group (e.g., a benzylcarbonyl

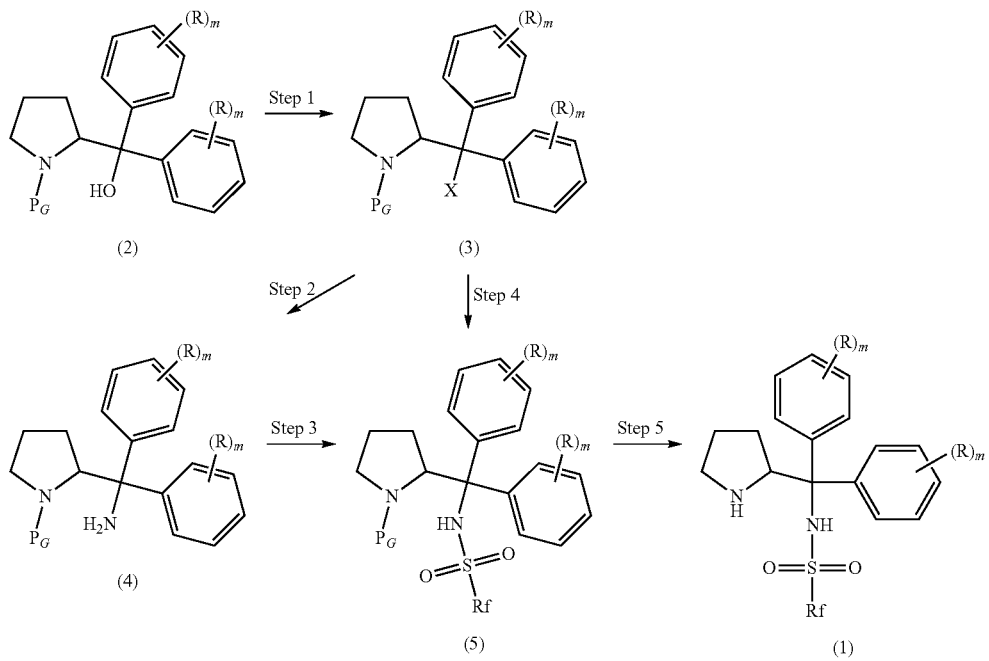

(wherein Rf, $P_G$, R and m are as defined above.)

group, a 1-phenylethylcarbonyl group, a 2-phenylethylcarbonyl group, a (naphthyl-1-yl)methylcarbonyl group, a (naphthyl-2-yl)methylcarbonyl group, a 1-(naphthyl-1-yl)ethylcarbonyl group, a 1-(naphthyl-2-yl)ethylcarbonyl group, a 2-(naphthyl-1-yl)ethylcarbonyl group, a 2-(naphthyl-2-yl)ethylcarbonyl group), a $C_7$-$C_{11}$ aryloxycarbonyl group (e.g., a phenoxycarbonyl group, a 1-naphthyloxycarbonyl group, a 2-naphthyloxycarbonyl group), a $C_8$-$C_{15}$ aralkyloxycarbonyl group (e.g., a benzyloxycarbonyl group, a 1-phenylethoxycarbonyl group, a 2-phenylethoxycarbonyl group, a (naphthyl-1-yl)methoxycarbonyl group, a (naphthyl-2-yl)methoxycarbonyl group, a 1-(naphthyl-1-yl)ethoxycarbonyl group, a 1-(naphthyl-2-yl)ethoxycarbonyl group, a 2-(naphthyl-1-yl)ethoxycarbonyl group, a 2-(naphthyl-2-yl)ethoxycarbonyl group), a $C_6$-$C_{10}$ arylsulfonyl group (e.g., a benzenesulfonyl group, a 1-naphthalenesulfonyl group, a 2-naphthalenesulfonyl group), a benzhydryl group, a trityl group, a tri-$C_1$-$C_6$ alkylsilyl group (e.g., trimethylsilyl group, a triethylsilyl group, a tert-butyldimethylsilyl group, a tert-butyldiethylsilyl group), a 9-fluorenylmethyloxycarbonyl group and a phthaloyl group. Each of the above-exemplified amino-group-protecting groups may be substituted by a halogen atom, a $C_1$-$C_6$ alkoxy group or a nitro group.

Specific examples of the amino-group-protecting group include an acetyl group, a trifluoroacetyl group, a pivaloyl group, a tert-butoxycarbonyl group, a 2,2,2-trichloroethoxycarbonyl group, a benzyl group, a benzyloxycarbonyl group, a 9-fluorenylmethyloxycarbonyl group, a benzhydryl group, a trityl group, a phthaloyl group, a p-toluenesulfonyl group and an o-nitrobenzenesulfonyl group.

The $C_6$-$C_{10}$ aryl group refers to an aromatic monocyclic or polycyclic (condensed) hydrocarbon group having 6 to 10 carbon atoms, and specific examples thereof include a phenyl group, a 1-naphthyl group and a 2-naphthyl group.

The $C_7$-$C_{14}$ aralkyl group refers to a group in which a $C_6$-$C_{10}$ aryl group is bound to a $C_{1-4}$ alkyl group, and specific examples thereof include a benzyl group, a 1-phenylethyl group, a 2-phenylethyl group, a (naphthyl-1-yl)methyl group, a (naphthyl-2-yl)methyl group, a 1-(naphthyl-1-yl)ethyl group, a 1-(naphthyl-2-yl)ethyl group, a 2-(naphthyl-1-yl)ethyl group and a 2-(naphthyl-2-yl)ethyl group.

The $C_7$-$C_{11}$ arylcarbonyl group refers to a group in which a $C_6$-$C_{10}$ aryl group is bound to —C(=O)—, and specific examples thereof include a benzoyl group, a 1-naphthoyl group and a 2-naphthoyl group.

The $C_8$-$C_{15}$ aralkylcarbonyl group refers to a group in which a $C_7$-$C_{14}$ aralkyl group is bound to —C(=O)—, and specific examples thereof include a benzylcarbonyl group, a 1-phenylethylcarbonyl group, a 2-phenylethylcarbonyl group, a (naphthyl-1-yl)methylcarbonyl group, a (naphthyl-2-yl)methylcarbonyl group, a 1-(naphthyl-1-yl)ethylcarbonyl group, a 1-(naphthyl-2-yl)ethylcarbonyl group, a 2-(naphthyl-1-yl)ethylcarbonyl group and a 2-(naphthyl-2-yl)ethylcarbonyl group.

The $C_7$-$C_{11}$ aryloxycarbonyl group refers to a group in which a $C_6$-$C_{10}$ aryl group is bound to —C(=O)O—, and specific examples thereof include a phenoxycarbonyl group, a 1-naphthyloxycarbonyl group and a 2-naphthyloxycarbonyl group.

The $C_8$-$C_{15}$ aralkyloxycarbonyl group refers to a group in which a $C_7$-$C_{14}$ aralkyl group is bound to —C(=O)O—, and specific examples thereof include a benzyloxycarbonyl group, a 1-phenylethyloxycarbonyl group, a 2-phenylethyloxycarbonyl group, a (naphthyl-1-yl)methyloxycarbonyl group, a (naphthyl-2-yl)methyloxycarbonyl group, a 1-(naphthyl-1-yl)ethyloxycarbonyl group, a 1-(naphthyl-2-yl)ethyloxycarbonyl group, a 2-(naphthyl-1-yl)ethyloxycarbonyl group and a 2-(naphthyl-2-yl)ethyloxycarbonyl group.

The tri-$C_1$-$C_6$ alkylsilyl group refers to a silyl group having "three $C_6$-$C_6$ alkyl groups", and specific examples thereof include a trimethylsilyl group, a triethylsilyl group, a tert-butyldimethylsilyl group and a tert-butyldiethylsilyl group.

$P_G$ is preferably a $C_7$-$C_{14}$ aralkyl group (preferably a benzyl group), a $C_2$-$C_7$ alkoxycarbonyl group (preferably a tert-butoxycarbonyl group), a $C_8$-$C_{15}$ aralkyloxycarbonyl group (preferably a benzyloxycarbonyl group) or a tri-$C_1$-$C_6$ alkylsilyl group (preferably a trimethylsilyl group) in each of which a $C_1$-$C_6$ alkyl group, a nitro group or a halogen atom may be bound on a benzene ring, and is particularly preferably a benzyl group.

[Step 1]

Step 1 is a step of producing compound (3) from compound (2), and compound (3) can be produced by converting a hydroxyl group in compound (2) to a leaving group.

Specific examples of the leaving group include a halogen atom, a $C_1$-$C_6$ alkanesulfonyloxy group (e.g., a methanesulfonyloxy group, an ethanesulfonyloxy group, a propanesulfonyloxy group), a $C_1$-$C_6$ perfluoroalkanesulfonyloxy group (e.g., a trifluoromethanesulfonyloxy group, a pentafluoroethanesulfonyloxy group, a heptafluoropropanesulfonyloxy group), and a $C_6$-$C_{10}$ arylsulfonyloxy group (e.g., a benzenesulfonyloxy group, a p-toluenesulfonyloxy group, a p-nitrobenzenesulfonyloxy group, an o-nitrobenzenesulfonyloxy group, a 1-naphthalenesulfonyloxy group, a 2-naphthalenesulfonyloxy group).

The leaving group is preferably a halogen atom, particularly preferably a chlorine atom.

The reaction for converting the hydroxyl group to the leaving group can be carried out by reacting a halogenating agent (e.g., thionyl chloride), a $C_1$-$C_6$ alkanesulfonylating agent (e.g., methanesulfonyl chloride), a $C_1$-$C_6$ perfluoroalkanesulfonylating agent (e.g., trifluoromethanesulfonyl chloride), a $C_{6-10}$ arylsulfonylating agent which may have a nitro group or the like (e.g., benzenesulfonyl chloride, p-toluenesulfonyl chloride, o-nitrobenzenesulfonyl chloride, p-nitrobenzenesulfonyl chloride) or the like with compound (2). The amount of the reagent to be used is preferably 1 to 10 moles, more preferably 1 to 3 moles, relative to 1 mole of compound (2), from the viewpoint of yield and economic performance.

The reaction may be carried out in the presence of a base. Specific examples of the base include: an inorganic base, such as sodium carbonate, potassium carbonate, cesium carbonate, sodium hydrogen carbonate and potassium hydrogen carbonate; and an organic base, such as pyridine, 2,6-lutidine, triethylamine, diisopropylethylamine, N-methylmorpholine, 1,8-diazabicyclo[5.4.0]undec-7-ene (DBU), 1,5-diazabicyclo[4.3.0]non-5-ene (DBN) and imidazole.

The amount of the base to be used is preferably 10 moles or less, more preferably 1 to 5 moles, relative to 1 mole of compound (2), from the viewpoint of yield and economic performance.

The reaction is preferably carried out in a solvent. Specific examples of the solvent include an aromatic hydrocarbon solvent (e.g., toluene, benzene, xylene); a halogenated hydrocarbon solvent (e.g., chloroform, dichloromethane, carbon tetrachloride); an ether solvent (e.g., diethyl ether, tetrahydrofuran (THF), 1,4-dioxane); an aprotic polar solvent (e.g., dimethylformamide (DMF), dimethylacetamide); and a solvent mixture of two or more of the above-mentioned solvents. Among these solvents, a halogenated hydrocarbon solvent is preferred, and chloroform is particularly preferred, from the viewpoint of achieving good reactivity and good yield. The amount of the solvent to be used is preferably 2 to 50 mL, more preferably 3 to 10 mL, relative to 1 g of compound (2).

For example, the reaction is carried out by a method in which a reagent such as a halogenating agent and a sulfonylating agent is added to a mixture of compound (2), the base and the solvent and then the resultant solution is mixed.

The reaction temperature may vary depending on the types of compound (2), the reagent, the base and the solvent, and is preferably within the range from −20 to 80° C., more preferably from −10 to 50° C.

The reaction time may vary depending on the types of compound (2), the reagent, the base and the solvent and the reaction temperature, and is preferably 0.5 to 24 hours, more preferably 1 to 6 hours.

The degree of progression of the reaction can be confirmed by an analysis means such as thin-layer chromatography, gas chromatography and high-performance liquid chromatography.

The isolation of compound (3) contained in a reaction mixture thus produced can be carried out by subjecting the reaction mixture to a work-up procedure (e.g., neutralization, extraction, washing with water, distillation, crystallization). The purification of compound (3) can be carried out by subjecting compound (3) to an extraction purification treatment, a distillation treatment, an adsorption treatment with activated carbon, silica, alumina or the like, or a chromatography treatment by silica gel column chromatography or the like. Compound (3) may be subjected to the subsequent step in the form of the reaction mixture. Particularly from the viewpoint of yield and economic performance, it is preferred to use the reaction mixture containing compound (3), which is produced in step 1, without any modification in the subsequent step.

[Step 2]

Step 2 is a step for producing compound (4) by the reaction of compound (3) with ammonia, and compound (4) can be produced by converting the leaving group in compound (3) to an amino group with ammonia.

Ammonia is generally used in the form of an aqueous solution or a solution in an alcohol (e.g., methanol, ethanol, isopropyl alcohol). Water or the alcohol may double as a solvent. The amount of ammonia to be used is preferably 2 to 200 moles, more preferably 5 to 100 moles, relative to 1 mole of compound (3), from the viewpoint of yield and economic performance.

For example, the reaction is carried out by a method in which ammonia is added to the reaction mixture containing compound (3) and then the resultant solution is mixed.

The reaction temperature may vary depending on the types of compound (3) and the solvent, and is preferably within the range from 0 to 80° C., more preferably from 10 to 50° C.

The reaction time may vary depending on the types of compound (3) and the solvent and the reaction temperature, and is preferably 0.5 to 24 hours, more preferably 1 to 8 hours.

The degree of progression of the reaction can be confirmed by an analysis means such as thin-layer chromatography, gas chromatography and high-performance liquid chromatography.

The isolation of compound (4) contained in a reaction mixture thus produced can be carried out by subjecting the reaction mixture to a work-up procedure (e.g., neutralization, extraction, washing with water, distillation, crystallization). The purification of compound (4) can be carried out by subjecting compound (4) to an extraction purification treatment, a distillation treatment, an adsorption treatment with activated carbon, silica, alumina or the like, or a chromatography treatment by silica gel column chromatography or the like. Compound (4) may be subjected to the subsequent step in the form of the reaction mixture.

[Step 3]

Step 3 is a step for producing compound (5) from compound (4), and compound (5) can be produced by reacting compound (4) with a $C_1$-$C_8$ perfluoroalkanesulfonylating agent (e.g., a trifluoromethanesulfonylating agent).

Specific examples of the $C_1$-$C_8$ perfluoroalkanesulfonylating agent include trifluoromethanesulfonyl chloride, trifluoromethanesulfonic anhydride, pentafluoroethanesulfonyl chloride and nonafluorobutanesulfonyl chloride. The amount of the $C_1$-$C_8$ perfluoroalkanesulfonylating agent to be used is preferably 1 to 2 moles, more preferably 1.05 to 1.4 moles, relative to 1 mole of compound (4), from the viewpoint of yield and economic performance.

The reaction is generally carried out in the presence of a base. Specific examples of the base include: an inorganic base, such as sodium carbonate, potassium carbonate, cesium carbonate, sodium hydrogen carbonate and potassium hydrogen carbonate; and an organic base, such as pyridine, 2, 6-lutidine, triethylamine, diisopropylethylamine, N-methylmorpholine, DBU, DBN and imidazole, preferably triethylamine. The amount of the base to be used is preferably 1 to 3 moles, more preferably 1.2 to 2 moles, relative to 1 mole of compound (4), from the viewpoint of yield and economic performance.

The reaction is generally carried out in a solvent. Specific examples of the solvent include an aromatic hydrocarbon solvent (e.g., toluene, benzene, xylene); a halogenated hydrocarbon solvent (e.g., chloroform, dichloromethane, carbon tetrachloride); an ether solvent (e.g., diethyl ether, THF); an aprotic polar solvent (e.g., DMF, dimethylacetamide); and a solvent mixture of two or more of the above-mentioned solvents. Among these solvents, a halogenated hydrocarbon solvent is preferred, and chloroform is particularly preferred, from the viewpoint of achieving good reactivity and good yield. The amount of the solvent to be used is preferably 3 to 50 mL, more preferably 5 to 25 mL, relative to 1 g of compound (4).

For example, the reaction is carried out by a method in which a trifluoromethanesulfonylating agent is added to a mixture of compound (4), the base and the solvent and then the resultant solution is mixed.

The reaction temperature may vary depending on the types of compound (4), the trifluoromethanesulfonylating agent, the base and the solvent, and is preferably within the range from −20 to 80° C., more preferably from −10 to 50° C.

The reaction time may vary depending on the types of compound (4), the trifluoromethanesulfonylating agent, the base and the solvent and the reaction temperature, and is preferably 1 to 24 hours, more preferably 3 to 12 hours.

The degree of progression of the reaction can be confirmed by an analysis means such as thin-layer chromatography, gas chromatography and high-performance liquid chromatography.

The isolation of compound (5) contained in a reaction mixture thus produced can be carried out by subjecting the reaction mixture to a work-up procedure (e.g., neutralization, extraction, washing with water, distillation, crystallization). The purification of compound (5) can be carried out by subjecting compound (5) to an extraction-purification procedure, a distillation procedure, an adsorption procedure with activated carbon, silica, alumina or the like, or a chromatography procedure by silica gel column chromatography or the like. Compound (5) may be subjected to the subsequent step in the form of the reaction mixture.

[Step 4]

Step 4 is a step for producing compound (5) by the reaction of compound (3) with trifluoromethanesulfonamide or a salt thereof.

An example of the salt of trifluoromethanesulfonamide is a lithium salt.

Compound (3) may be used in the form of the reaction mixture produced in step 1. In this case, it is desirable to remove the remaining halogenating agent.

The amount of the trifluoromethanesulfonamide or a salt thereof to be used is preferably 0.8 to 3 moles, more preferably 1.1 to 2 moles, relative to 1 mole of compound (3), from the viewpoint of yield and economic performance.

The reaction is generally carried out in the presence of a base. Specific examples of the base include: an inorganic base, such as sodium carbonate, potassium carbonate, cesium carbonate, sodium hydrogen carbonate and potassium hydrogen carbonate; and an organic base, such as pyridine, 2, 6-lutidine, triethylamine, diisopropylethylamine, N-methylmorpholine, DBU, DBN and imidazole. The amount of the base to be used is preferably 1 to 10 moles, more preferably 1.2 to 5 moles, relative to 1 mole of compound (3), from the viewpoint of yield and economic performance.

The reaction is preferably carried out in a solvent. Specific examples of the solvent include an aromatic hydrocarbon solvent (e.g., toluene, benzene, xylene); a halogenated hydrocarbon solvent (e.g., chloroform, dichloromethane, carbon tetrachloride); an ether solvent (e.g., diethyl ether, tetrahydrofuran, 1,4-dioxane); an aprotic polar solvent (e.g., DMF, dimethylacetamide); and a solvent mixture of two or more of the above-mentioned solvents. Among these solvents, a halogenated hydrocarbon solvent is preferred, and chloroform is particularly preferred, from the viewpoint of achieving good reactivity and good yield. The amount of the solvent to be used is preferably 2 to 100 mL, more preferably 2.5 to 10 mL, relative to 1 g of compound (3).

For example, the reaction is carried out by a method in which trifluoromethanesulfonamide or a salt thereof and the base are added to a mixture of compound (3) and the solvent and then the resultant solution is mixed.

The reaction temperature may vary depending on the types of compound (3), the base and the solvent, and is preferably within the range from 0 to 120° C., more preferably from 20 to 80° C.

The reaction time may vary depending on the types of compound (3), the base and the solvent and the reaction temperature, and is preferably 0.5 to 24 hours, more preferably 1 to 8 hours.

The degree of progression of the reaction can be confirmed by an analysis means such as thin-layer chromatography, gas chromatography and high-performance liquid chromatography.

The isolation of compound (5) contained in a reaction mixture thus produced can be carried out by subjecting the reaction mixture to a work-up procedure (e.g., neutralization, extraction, washing with water, distillation, crystallization). The purification of compound (5) can be carried out by subjecting compound (5) to an extraction-purification procedure, a distillation procedure, an adsorption procedure with activated carbon, silica, alumina or the like, or a chromatography procedure by silica gel column chromatography or the like. Compound (5) may be subjected to the subsequent step in the form of the reaction mixture.

[Step 5]

Step 5 is a step for producing compound (1) by deprotecting compound (5).

The deprotection can be carried out by, for example, a known method disclosed in "Protective Groups in Organic Synthesis", attributed to T. W. Greene and P. G. M. Wuts (published by Wiley-Interscience, fourth edition, 2006).

Hereinbelow, this step will be described concretely by employing a case where $P_G$ is a $C_{7-14}$ aralkyl group.

In the case where $P_G$ is a $C_{7-14}$ aralkyl group, the deprotection can be carried out by reacting compound (5) in the presence of a catalyst and a hydrogen source.

Specific examples of the catalyst include palladium-carbon, palladium black, palladium chloride, palladium hydroxide, rhodium-carbon, platinum oxide, platinum black, platinum-palladium, raney nickel and raney cobalt. The amount of the catalyst to be used is preferably 0.001 to 0.5 g, more preferably 0.05 to 0.15 g, relative to 1 g of compound (5), from the viewpoint of yield and economic performance.

Specific examples of the hydrogen source include a hydrogen gas, ammonium formate and cyclohexadiene.

The amount of the hydrogen source to be used is preferably 1 to 5 moles, more preferably 1 to 3 moles, relative to 1 mole of compound (5). In the case where a hydrogen gas is used, the hydrogen gas is generally used under a pressure of 0.1 to 1.0 Mpa, due to the limitation with respect to experimental facilities.

The reaction is carried out in a solvent. Specific examples of the solvent include an aromatic hydrocarbon solvent (e.g., toluene, benzene, xylene); an aliphatic hydrocarbon solvent (e.g., hexane, heptane, cyclohexane); an alcohol solvent (e.g., methanol, ethanol); an ether solvent (e.g., diethyl ether, THF); an ester solvent (e.g., ethyl acetate, isopropyl acetate); water; or a mixture of two or more of these solvents. Among these solvents, an alcohol solvent is preferred, and methanol is particularly preferred, from the viewpoint of achieving good reactivity and good yield.

The reaction is carried out by a method in which the compound (5), the catalyst and the solvent are mixed together, then the hydrogen source is added to the resultant mixture and then the resultant solution is mixed, or the like.

The reaction temperature may vary depending on the types of compound (5), the catalyst, the hydrogen source and the solvent, and is preferably within the range from 0 to 60° C., more preferably from 10 to 50° C.

The reaction time may vary depending on the types of compound (5), the catalyst, the hydrogen source and the solvent and the reaction temperature, and is preferably 1 to 20 hours, more preferably 1 to 10 hours.

The degree of progression of the reaction can be confirmed by an analysis means such as thin-layer chromatography, gas chromatography and high-performance liquid chromatography.

The isolation of compound (1) contained in a reaction mixture thus produced can be carried out by subjecting the reaction mixture to a work-up procedure (e.g., neutralization, extraction, washing with water, distillation, crystallization). The purification of compound (1) can be carried out by subjecting compound (1) to an extraction-purification procedure, a distillation procedure, an adsorption procedure with activated carbon, silica, alumina or the like, or a chromatography procedure by silica gel column chromatography or the like.

Compound (2) to be used in the production of compound (1) can be produced through, for example, the following route. When the reaction is carried out with starting with optically active proline, an optically active form of compound (2) can be produced.

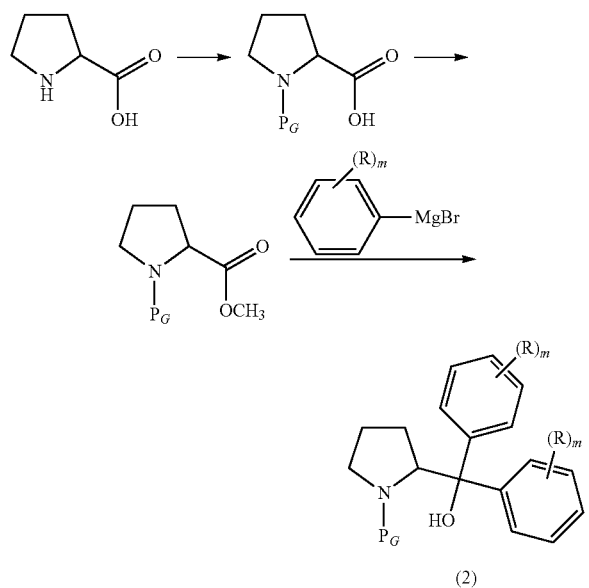

In this production, J. Org. Chem., 76, 1513 (2011), Adv. Synth. Catal., 350, 1781 (2008), J. Am. Chem. Soc., 125, 5501 (2003), Synthesis 2010, 1394 and the like can be referred.

Compound (1) can be used in an aldol reaction as shown below. Particularly, an optically active form of compound (1) can be used in an asymmetric aldol reaction to produce an optically active form of compound (III).

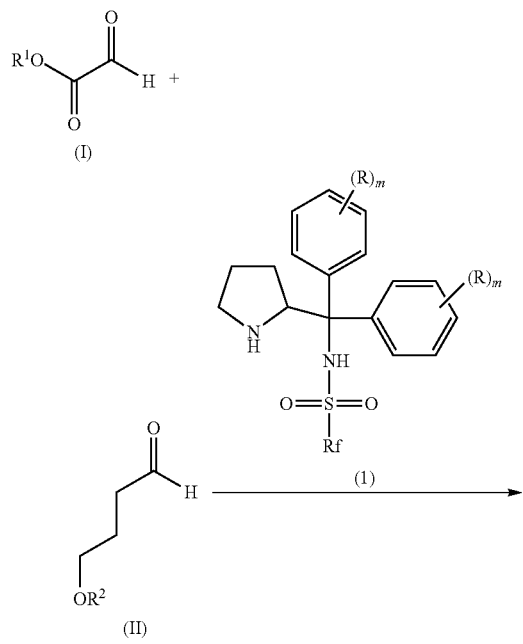

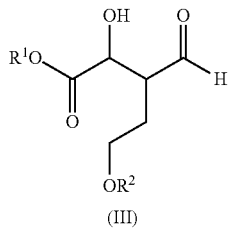

Examples of the protecting group for a carboxyl group (hereinafter referred to as "carboxyl-group-protecting group") represented by $R^1$ include a $C_1$-$C_6$ alkyl group, a $C_7$-$C_{14}$ aralkyl group, a phenyl group, a trityl group and a tri-$C_1$-$C_6$ alkylsilyl group, and specific example thereof include a methyl group, an ethyl group, a tert-butyl group, a benzyl group, a trityl group, a trimethylsilyl group, a triethylsilyl group, a tert-butyldimethylsilyl group and a tert-butyldiethylsilyl group.

$R^1$ is preferably a $C_1$-$C_6$ alkyl group, more preferably a $C_1$-$C_4$ alkyl group, particularly preferably an ethyl group.

Specific examples of the protecting group for a hydroxyl group (hereinafter referred to as "hydroxyl-group-protecting group") represented by $R^2$ include a $C_1$-$C_6$ alkyl group, a phenyl group, a trityl group, a $C_7$-$C_{14}$ aralkyl group, a formyl group, a $C_2$-$C_7$ alkylcarbonyl group, a benzoyl group, a $C_8$-$C_{15}$ aralkylcarbonyl group, a 2-tetrahydropyranyl group, a 2-tetrahydrofuranyl group, a tri-$C_1$-$C_6$ alkylsilyl group, a succinimidoxycarbonyl group, a $C_7$-$C_{11}$ arylcarbonyl group, a $C_7$-$C_{11}$ aryloxycarbonyl group and a $C_8$-$C_{15}$ aralkyloxycarbonyl group. Each of these groups may have a halogen atom, a $C_1$-$C_6$ alkyl group, a $C_1$-$C_6$ alkoxy group, a carboxyl group, a nitro group or the like.

Specific examples of the hydroxyl-group-protecting group include a benzyl group, an acetyl group, a trimethylsilyl group, a triethylsilyl group, a tert-butyldimethylsilyl group, a tert-butyldiethylsilyl group, a succinimidoxycarbonyl group, a phenoxycarbonyl group and a benzyloxycarbonyl group.

$R^2$ is preferably a $C_7$-$C_{14}$ aralkyl group, particularly preferably a benzyl group.

The above-mentioned aldol reaction is a reaction in which compound (I), which is a glyoxylic acid derivative, or a polymer thereof with compound (II) in the presence of compound (1) to produce compound (III).

The polymer of compound (I) is a compound represented by formula (I-1):

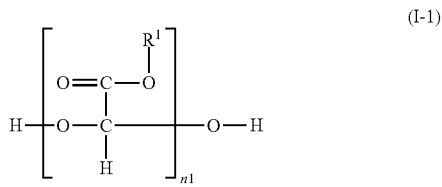

(wherein n1 represents an integer of 2 or more; and $R^1$ is as defined above)

or a cyclic polymer compound, and a typical example of the cyclic polymer compound is a trimer represented by the following formula:

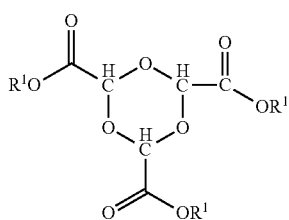

(wherein R¹ is as defined above).

Compound (I) is commercially available, and a commercially available product can be used without any modification. Each of compound (I) and a polymer thereof is also commercially available in the form of a solution (e.g., a solution in toluene (also referred to as a "toluene solution", hereinafter)), and the commercially available toluene solution can be used without any modification. In the case where a solvent other than toluene is used, it is possible to concentrate the toluene solution and replace the solvent by another solvent upon use.

The aldol reaction is preferably carried out in a solvent. Examples of the solvent include: an aromatic hydrocarbon solvent (e.g., toluene, benzene, xylene); an aliphatic hydrocarbon solvent (e.g., hexane, heptane, cyclohexane); an alcohol solvent (e.g., methanol, ethanol, 2-propanol, 2-methyl-2-propanol); a halogenated hydrocarbon solvent (e.g., chloroform, dichloromethane, carbon tetrachloride, 1-chlorobutane); an ether solvent (e.g., diethyl ether, THF, 2-methyltetrahydrofuran, 1,2-dimethoxyethane (ethylene glycol dimethyl ether (EGDE)), methyl tert-butyl ether, ethyl tert-butyl ether, diisopropyl ether, dibutyl ether, cyclopentyl methyl ether, 1,4-dioxane, bis(2-methoxy ethyl)ether); an ester solvent (e.g., ethyl acetate, isopropyl acetate); a ketone solvent (e.g., acetone, 2-butanone, 3-pentanone); a nitrile solvent (e.g., acetonitrile, propionitrile); an aprotic polar solvent (e.g., DMF, dimethylacetamide, dimethyl sulfoxide, N-methylpyrrolidone (NMP), 1,3-dimethyl-2-imidazolidinone (DMI)); water; and a solvent mixture of the aforementioned solvents.

In the asymmetric aldol reaction using an optically active form of the compound (1), from the viewpoint of enantioselectivity and diastereoselectivity, an aromatic hydrocarbon solvent; an alcohol solvent; a halogenated hydrocarbon solvent; an ether solvent; a nitrile solvent; water; a solvent mixture of the aforementioned solvents, and the like are preferred. From the viewpoint of achieving particularly superior yield, enantioselectivity and diastereoselectivity, it is preferred to use at least one solvent selected from the group consisting of NMP, DMI, DMF, acetonitrile, THF, EGDE, toluene, chloroform, methanol and water, it is more preferred to use a mixture of two solvents selected from the aforementioned solvents, and it is particularly preferred to use a solvent mixture of water and NMP or water and DMI.

The amount of compound (I) to be used is preferably 0.5 to 10 moles, more preferably 0.8 to 2 moles, relative to 1 mole of compound (II), from the viewpoint of economic performance.

The aldol reaction can be carried out by: a method in which compound (II), compound (1) and the solvent are added to a polymer of compound (I) and the resultant solution is mixed; a method in which a polymer of compound (I), compound (1) and the solvent are mixed together, then compound (II) is added to the solution, and the resultant solution is mixed; a method in which compound (II), compound (1) and the solvent are mixed together, then a polymer of compound (I) is added to the solution, and the resultant solution is mixed; and the like. From the viewpoint of yield and selectivity, it is preferred to carry out the aldol reaction by: a method in which compound (II), compound (1) and the solvent are mixed together, then a polymer of compound (I) is added to the solution and then the resultant solution was mixed; or a method in which a polymer of compound (I), compound (1) and the solvent are mixed together, then the compound (II) is added to the solution and then the resultant solution is mixed.

The amount of compound (1) to be used is preferably 0.1 to 30 mol %, more preferably 0.5 to 15 mol %, relative to the amount of compound (II), from the viewpoint of yield and economic performance.

The reaction temperature may vary depending on the types of compound (II), and is preferably within the range from −20 to 100° C., more preferably from −10 to 40° C.

The reaction time may vary depending on the types of compound (II) and the reaction temperature, and is preferably 1 to 100 hours, more preferably 3 to 50 hours.

The degree of progression of the reaction can be confirmed by an analysis means such as thin-layer chromatography, gas chromatography and high-performance liquid chromatography.

The isolation of compound (III) contained in a reaction mixture thus produced can be carried out by subjecting the reaction mixture to a work-up procedure (e.g., neutralization, extraction, washing with water, distillation, crystallization). The purification of compound (III) can be carried out by subjecting compound (III) to an extraction-purification procedure, a distillation procedure, an adsorption procedure with activated carbon, silica, alumina or the like, or a chromatography procedure by silica gel column chromatography or the like.

In the case where the asymmetric aldol reaction is carried out using an optically active form of compound (1), from the viewpoint of diastereoselectivity, it is preferred to use an optically active form of compound (1) in which m is 0 or an optically active form of compound (1) in which R is a methyl group, an ethyl group or a trifluoromethyl group depending on the types of compound (II), and it is particularly preferred to use an optically active form of compound (1) in which m is 0.

According to the asymmetric aldol reaction, an optically active form of the anti-form compound (III), i.e., a compound represented by formula (IIIR) (hereinafter referred to as "compound (IIIR)") or a compound represented by formula (IIIS) (hereinafter referred to as "compound (IIIS)"):

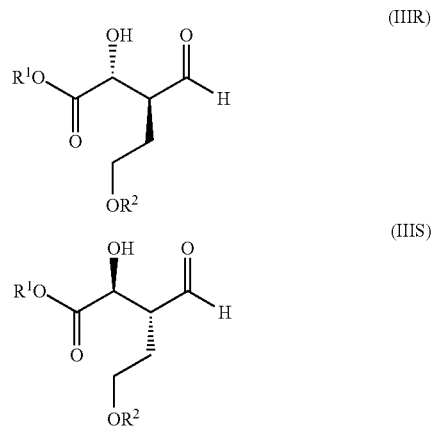

can be produced preferentially. Compound (IIIR) is produced preferentially in the case where an S-form of compound (1) is used as a catalyst, while compound (IIIS) is produced preferentially in the case where an R-form of compound (1) is used as a catalyst, wherein the diastereomer ratio (i.e., a syn/anti ratio) can become 50/50 or more. It becomes possible to achieve such selectivity that the diastereomer ratio (syn/anti ratio) is 20/80 or more, more preferably 10/90 or more.

In the case where an optically active form of the compound (1) is used as a catalyst, the enantiomeric excess can become 50 ee % or more. It becomes possible to achieve such selectivity that the enantiomeric excess is 80 ee % or more, more preferably 90 ee % or more.

The isomerization of an optically active form of compound (III) sometimes occurs during the isolation or purification of the optically active form from the reaction mixture. Therefore, it is desirable to measure the diastereomer ratio (syn/anti ratio) and the enantiomeric excess (ee(%)) of an optically active form of compound (III) after the aldol reaction without performing isolation or purification, i.e., after the optically active form of compound (III) is converted to a compound that never undergoes isomerization. For example, it is desirable to convert an optically active form of compound (III) to an optically active form of a corresponding acetal compound, i.e., a compound represented by formula (IV):

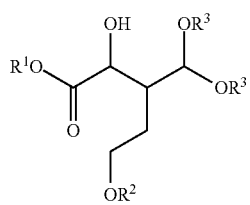

(IV)

(wherein $R^1$ and $R^2$ are as defined above; and $R^3$ represents a $C_1$-$C_{12}$ alkyl group, a $C_2$-$C_{12}$ alkenyl group, a $C_2$-$C_{12}$ alkynyl group or a $C_7$-$C_{14}$ aralkyl group)
(hereinafter referred to as "compound (IV)").

$R^3$ is preferably a $C_1$-$C_{12}$ alkyl group, more preferably a $C_1$-$C_8$ alkyl group, still more preferably a $C_1$-$C_4$ alkyl group, still more preferably a $C_1$-$C_3$ alkyl group, particularly preferably a methyl group.

An optically active form of compound (IV) can be produced by reacting a reaction mixture (which contains an optically active form of compound (III) and is obtained after the completion of the asymmetric aldol reaction) or an optically active form of compound (III) (which is isolated but is not purified yet) with an alcohol compound represented by the following formula:

(wherein $R^3$ is as defined above) or an orthoformate compound represented by the following formula:

(wherein $R^3$ is as defined above)
in the presence of an acid catalyst.

Hereinbelow, the reaction with an alcohol compound represented by formula: $R^3OH$ will be described in more detail.

The amount of the alcohol compound to be used is preferably 2 to 200 moles, more preferably 10 to 100 moles, relative to 1 mole of the optically active form of compound (III), from the viewpoint of yield and economic performance. The alcohol compound is generally used as a reaction solvent.

Specific examples of the acid catalyst include pyridinium p-toluenesulfonate, and p-toluenesulfonic acid or a monohydrate thereof. From the viewpoint of reaction selectivity, pyridinium p-toluenesulfonate is preferred.

The amount of the acid catalyst to be used is preferably 0.01 to 1 moles, more preferably 0.01 to 0.1 moles, relative to 1 mole of the optically active form of compound (III), from the viewpoint of reactivity and economic performance.

The reaction can be carried out by: a method in which an alcohol compound and an acid catalyst are added to an optically active form of compound (III), which is isolated but is not purified yet, and then the resultant solution is mixed; a method in which an acid catalyst is added to an optically active form of compound (III), which is isolated but is not purified yet, then an alcohol compound is added to the solution, and the resultant solution is mixed; or the like. From the viewpoint of simplifying the operations, it is preferred to carry out the reaction by a method in which an alcohol compound and an acid catalyst are added to an optically active form of compound (III), which is isolated but is not purified yet, and then the resultant solution is mixed.

The reaction temperature may vary depending on the types of the alcohol compound and the acid catalyst, and is preferably within the range from 0 to 100° C., more preferably from 20 to 80° C., particularly preferably from 40 to 60° C.

The reaction time may vary depending on the types of the alcohol compound and the acid catalyst and the reaction temperature, and is preferably 10 minutes to 50 hours, more preferably 30 minutes to 20 hours, particularly preferably 1 to 10 hours.

The degree of progression of the reaction can be confirmed by an analysis means such as thin-layer chromatography, gas chromatography and high-performance liquid chromatography.

Next, the reaction with an orthoformate compound represented by the formula: $HC(OR^3)_3$ will be described in more detail.

The amount of the orthoformate compound to be used is preferably 1 to 50 moles, more preferably 3 to 30 moles, relative to 1 mole of the optically active form of compound (III), from the viewpoint of yield and economic performance.

Specific examples of the acid catalyst include p-toluenesulfonic acid or a monohydrate thereof and pyridinium p-toluenesulfonate. From the viewpoint of yield and economic performance, p-toluenesulfonic acid or a monohydrate thereof is preferred.

The amount of the acid catalyst to be used is preferably 0.01 to 1 mole, more preferably 0.01 to 0.2 mole, relative to 1 mole of the optically active form of compound (III), from the viewpoint of the reaction rate.

The reaction can be carried out by: a method in which an orthoformate compound and an acid catalyst are added to a reaction mixture containing an optically active form of compound (III), which is obtained after the completion of the asymmetric aldol reaction, and then the resultant solution is mixed; a method in which an acid catalyst is added to a reaction mixture containing an optically active form of compound (III), which is obtained after the completion of the aldol reaction, then an orthoformate compound is added to the solution, and the resultant solution is mixed; or the like. From the viewpoint of simplifying the operations, it is preferred to carry out the reaction by a method in which an orthoformate compound and an acid catalyst are added to a reaction mixture containing an optically active form of compound (III), which is obtained after the completion of the asymmetric aldol reaction, and then the resultant solution is mixed.

The reaction temperature may vary depending on the types of the orthoformate compound and the acid catalyst, and is preferably within the range from 0 to 100° C., more preferably from 10 to 40° C., particularly preferably from 20 to 30° C.

The reaction time may vary depending on the types of the orthoformate compound and the acid catalyst and the reaction temperature, and is preferably 10 minutes to 50 hours, more preferably 30 minutes to 20 hours, particularly preferably 1 to 10 hours.

The degree of progression of the reaction can be confirmed by an analysis means such as thin-layer chromatography, gas chromatography and high-performance liquid chromatography.

The isolation of the optically active form of compound (IV), which is contained in a mixture produced by the reaction with the alcohol compound or the orthoformate compound, can be carried out by subjecting the reaction mixture to a work-up procedure (e.g., neutralization, extraction, washing with water, distillation, crystallization). The purification of the optically active form of compound (IV) can be carried out by subjecting the optically active form of compound (IV) to a recrystallization procedure, an extraction-purification procedure, a distillation procedure, an adsorption procedure with activated carbon, silica, alumina or the like, or a chromatography procedure by silica gel column chromatography or the like.

The optically active form of compound (IV) thus produced is measured with respect to the diastereomer ratio (syn/anti ratio) and enantiomeric excess thereof. The measured diastereomer ratio (syn/anti ratio) and enantiomeric excess correspond to those of the optically active form of the compound (III).

EXAMPLES

Hereinbelow, the present invention will be described specifically by way of examples.

Ethyl glyoxylate was used in the form of a 50.8% toluene solution of a polymer purchased from JIAXING JLIGHT. All of liquid aldehydes and solvents other than ethyl glyoxylate were distilled before use.

All of reactions were carried out under an argon atmosphere and were monitored by thin-layer chromatography using MERCK 60 $F_{254}$ pre-coated silica gel plate (0.25 mm thick) Preparative thin-layer chromatography was carried out using Wakogel B-5F purchased from Wako Pure Chemical Industries Ltd. (Tokyo, Japan). Flash chromatography was carried out using silica gel 60N manufactured by Kanto Chemical Co., Inc. (Tokyo, Japan).

FT-IR spectra were measured with JASCO FT/IR-410 spectrometer.

$^1$H-NMR spectra were measured with Bruker AM400 (400 MHz) device, and were shown in terms of chemical shifts (δ ppm), multiplicities (s=singlet, d=doublet, t=triplet, q=quartet, m=multiplet), coupling constants (Hz), integral values and assignments.

HPLC analysis was carried out using CHIRALCEL OB-H (0.46 cm×25 cm), CHIRALPAK IA (0.46 cm×25 cm) and CHIRALPAK IB (0.46 cm×25 cm) while monitoring the UV detection with HITACHI Elite LaChrom Series HPLC.

Example 1-1

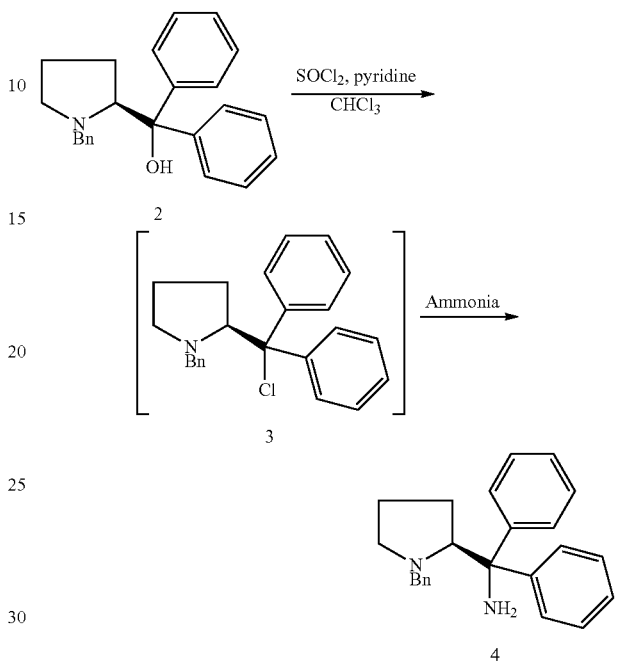

(1-1) A mixture of a compound 2 (19 g, 55 mmol), pyridine (8.7 g, 110 mmol) and chloroform (110 mL) was cooled to 0° C., and then thionyl chloride (9.8 g, 6 mL, 82.5 mmol) was added dropwise to the mixture. After 2 hours, a 28% aqueous ammonia solution (275 mL) was added to the resultant mixture at 0° C., and then the mixture was stirred at room temperature overnight. An organic layer was separated, and an aqueous layer was extracted with chloroform (2×110 mL). A residue produced by concentrating the combined organic layers was dissolved in methyl tert-butyl ether (MTBE) (220 mL), and was then washed with water (220 mL). The MTBE solution was extracted with 1 M hydrochloric acid (220 mL), and an aqueous layer was washed with MTBE (2×220 mL). The aqueous layer was made basic with a 28% aqueous ammonia solution, and was then extracted with MTBE (2×220 mL). The combined MTBE layers were dried over anhydrous sodium sulfate, and concentrated under reduced pressure. The residue was purified by flash column chromatography to produce a compound 4 as a yellow solid material (7.9 g, 42%).

(1-2) A mixture of a compound 2 (10.3 g, 30 mmol), pyridine (5.9 g, 75 mmol) and chloroform (60 mL) was cooled to 0° C., and then thionyl chloride (5.4 g, 45 mmol) was added dropwise to the mixture. After 2 hours, 2 M ammonia/isopropyl alcohol (150 mL) was added to the mixture at 0° C., and the resultant mixture was stirred at room temperature for 4 hours. Water (300 mL) and MTBE (300 mL) were added to the reaction mixture, and the resultant solution was separated. An organic layer was washed with water (2×300 mL), dried over anhydrous magnesium sulfate, and then concentrated under reduced pressure. The residue was purified by flash column chromatography to produce a compound 4 as a yellow solid material (4.4 g, 43%).

$^1$H NMR (CDCl$_3$, 400 Mz) δ 7.57-7.53 (m, 4H), 7.31-7.27 (m, 2H), 7.23-7.15 (m, 6H), 7.08-7.04 (m, 3H), 3.87 (dd, 1H, J=10.0, 3.7 Hz), 2.95 (d, 1H, J=12.7 Hz), 2.88 (d, 1H, J=12.7 Hz), 2.88-2.84 (m, 1H), 2.28-2.09 (m, 4H), 1.79-1.74 (m, 1H), 1.68-1.50 (m, 2H)

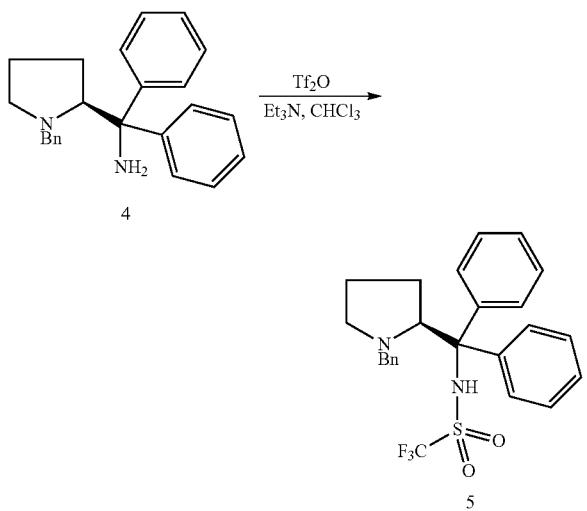

(2) A mixture of a compound 4 (7.5 g, 21.9 mmol), triethylamine (3.3 g, 32.9 mmol) and chloroform (66 mL) was cooled to 0° C., and then trifluoromethanesulfonic anhydride (7.4 g, 26.3 mmol) was added dropwise to the mixture. The mixture was stirred for 15 hours while raising the temperature of the mixture to room temperature. A saturated aqueous sodium hydrogen carbonate solution (66 mL) was added to the reaction mixture to terminate the reaction, and then the resultant solution was separated. An organic layer was washed with brine (66 mL) and water (66 ml) sequentially, and a washed solution was dried over anhydrous sodium sulfate, and concentrated under reduced pressure. The residue was purified by flash column chromatography to produce a compound 5 as a brown foam material (6.6 g, 64%).

$^1$H NMR (CDCl$_3$, 400 Mz) δ 7.44-7.40 (m, 4H), 7.35-7.20 (m, 12H), 4.04 (dd, 1H, J=9.5, 3.2 Hz), 3.30 (s, 2H), 2.37-2.27 (m, 3H), 2.11-2.04 (m, 1H), 1.73-1.63 (m, 1H), 1.35-1.22 (m, 1H)

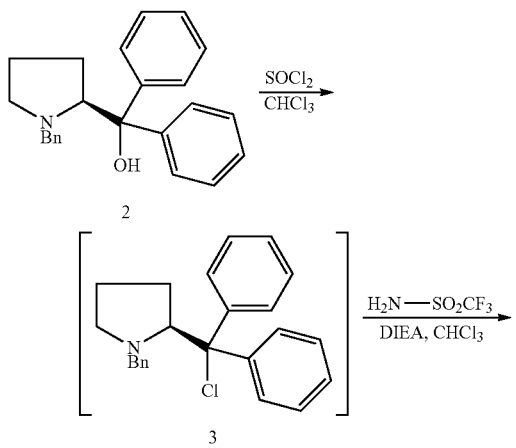

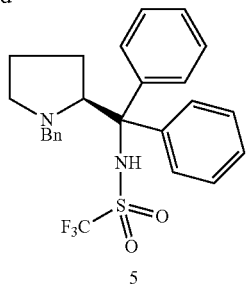

(2') A mixture of a compound 2 (10 g, 29.1 mmol) and chloroform (30 mL) was cooled to 0° C., and then thionyl chloride (34.6 g, 291 mmol) was added dropwise to the mixture. The mixture was heated to 45° C., was then stirred for 1 hour, was then allowed to cool, and was then stirred for 12 hours. Toluene (58 mL) was added to the mixture, and the solvent was distilled away under reduced pressure. A solution prepared by adding chloroform (30 mL) to the residue was added dropwise to a solution of diisopropylethylamine (18.8 g, 145.5 mmol) and trifluoromethanesulfonamide (8.7 g, 58.2 mmol) in chloroform (30 mL), the resultant mixture was stirred for 4 hours, then water (150 mL) was added to the mixture, and the resultant mixture was extracted with ethyl acetate (3×150 mL). An organic layer was dried over anhydrous sodium sulfate, and concentrated under reduced pressure. The residue was purified by flash column chromatography to produce a compound 5 as a brown foam material (7.6 g, 55%).

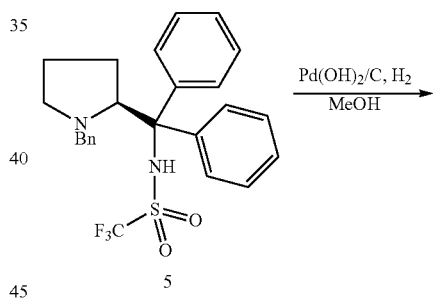

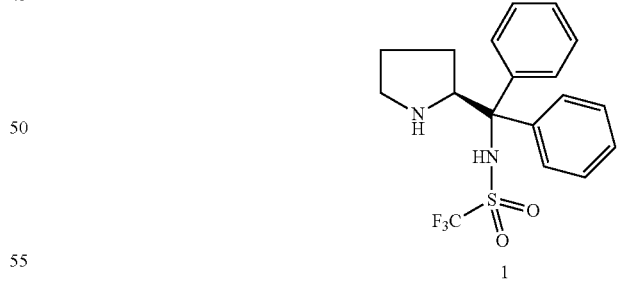

(3) 20% Pd(OH)$_2$/C (1.1 g, Lot OH-2002, KAWAKEN) was added to a suspension of a compound 5 (4.3 g, 9.1 mmol) in methanol 46 mL), and the resultant mixture was subjected to a hydrogenation reaction at 30° C. for 2 hours in an autoclave (0.5 MPa). The disappearance of the raw materials was confirmed by thin-layer chromatography. The reaction mixture was filtrated, then a filtrate was concentrated under reduced pressure, and the residue was dissolved in DMF (6.5 mL). Ethyl acetate (86 mL) was added to the solution, and the resultant mixture was heated at 60° C. for 1 hour. The mixture was cooled to room temperature, and then allowed to leave in a refrigerator for 14 hours. Crystals obtained by filtration were washed with ethyl acetate (3×30 mL), and the washed solution was dried under reduced pressure to produce a desired compound 1 as a white solid material (3.0 g, 85%).

$^1$H NMR (CD$_3$OD, 400 MHz) δ7.49-7.46 (m, 2H), 7.40-7.38 (m, 2H), 7.31-7.14 (m, 6H), 4.73-4.69 (m, 1H), 3.21-3.17 (m, 2H), 2.34-2.24 (m, 1H), 2.06-1.84 (m, 3H).

Example 1-2

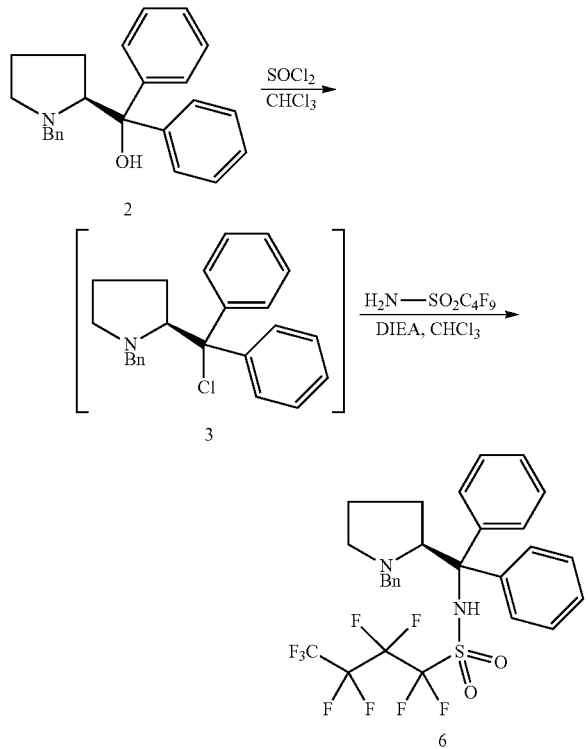

A mixture of a compound 2 (5.2 g, 15.0 mmol) and chloroform (20 mL) was cooled to 0° C., and then thionyl chloride (17.8 g, 150 mmol) was added dropwise to the mixture. The resultant mixture was stirred at room temperature for 15 hours, then toluene (20 mL) was added to the mixture, and then the solvent was distilled away under reduced pressure. A solution prepared by adding chloroform (20 mL) to the residue was added dropwise to a solution of diisopropylethylamine (9.7 g, 75 mmol) and nonafluorobutane sulfonamide (4.9 g, 16.5 mmol) in chloroform (20 mL), then the mixture was stirred for 4 hours, and then a saturated aqueous ammonium chloride solution (100 mL) was added to the mixture. An organic layer was separated and then washed with saturated aqueous sodium bicarbonate (50 mL), brine (50 mL) and water (50 mL) sequentially, then the washed solution was dried over anhydrous sodium sulfate, and concentrated under reduced pressure. The residue was purified by flash column chromatography to produce a compound 6 as a yellow solid material (5.5 g, 68%).

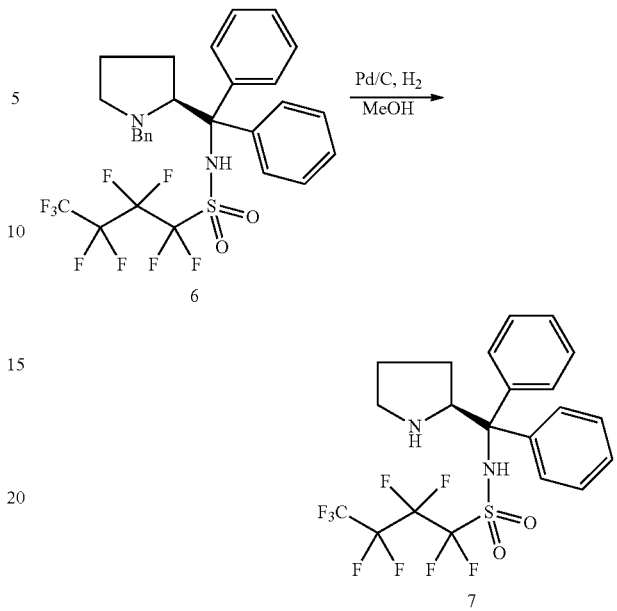

20% Pd(OH)$_2$/C (0.7 g, Lot OH-2002, KAWAKEN) was added to a solution of a compound 6 (3.0 g, 4.8 mmol) in methanol (30 mL), and the resultant mixture was subjected to a hydrogenation reaction at 30° C. for 2 hours in an autoclave (0.5 MPa). The reaction mixture was filtrated, and a filtrate was concentrated under reduced pressure. The residue was purified by flash column chromatography to produce a compound 7 as a white solid material (1.7 g, 66%).

$^1$H NMR (CD$_3$OD, 400 MHz) δ 7.50-7.47 (m, 2H), 7.41-7.39 (m, 2H), 7.30-7.14 (m, 6H), 4.70-4.67 (m, 1H), 3.22-3.19 (m, 2H), 2.36-2.24 (m, 1H), 2.06-1.84 (m, 3H).

Example 1-3

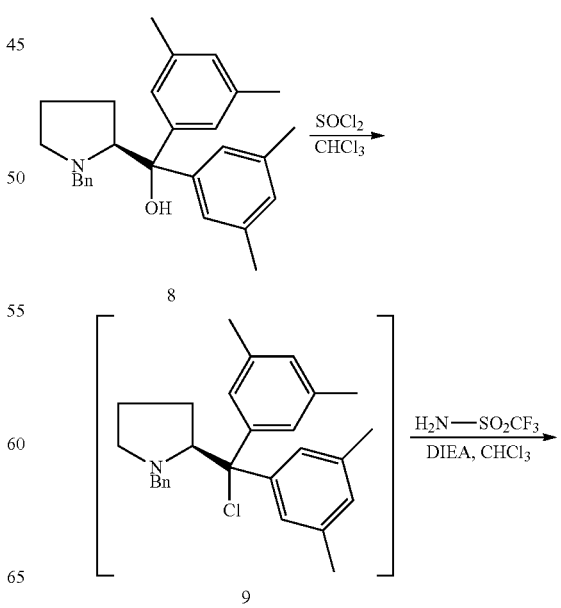

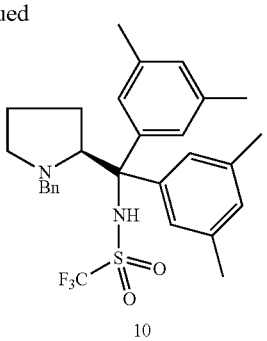

10

A mixture of a compound 8 (2.0 g, 5.0 mmol) and chloroform (10 mL) was cooled to 0° C., and then thionyl chloride (5.9 g, 50 mmol) was added dropwise to the mixture. The resultant mixture was stirred for 15 hours, and then the solvent was distilled away under reduced pressure. A solution prepared by adding chloroform (10 mL) to the residue was added dropwise to a solution of diisopropylethylamine (3.2 g, 25 mmol) and trifluoromethanesulfonamide (1.5 g, 10.0 mmol) in chloroform (10 mL), then the mixture was stirred for 4 hours, and then a saturated aqueous ammonium chloride solution (50 mL) was added to the mixture. An organic layer was separated and then washed with a saturated aqueous sodium bicarbonate (50 mL), brine (50 mL) and water (50 mL) sequentially, and the washed solution was dried over anhydrous sodium sulfate, and concentrated under reduced pressure. The residue was purified by flash column chromatography to produce a compound 10 as a brown solid material (0.5 g, 20%).

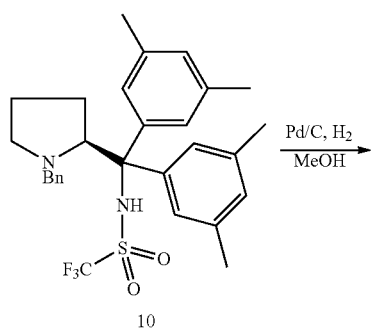

10

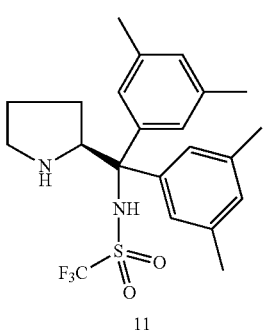

11

20% Pd(OH)$_2$/C (94 mg, Lot OH-2002, KAWAKEN) was added to a solution of a compound 10 (0.4 g, 0.75 mmol) in methanol (10 mL), and the resultant mixture was subjected to a hydrogenation reaction at 30° C. for 2 hours in an autoclave (0.5 MPa). The reaction mixture was filtrated, and a filtrate was concentrated under reduced pressure. The residue was purified by flash column chromatography to produce a compound 11 (247.8 mg, 75%).

$^1$H NMR ((CD$_3$)$_2$SO, 400 MHz) δ 7.09 (s, 2H), 6.96 (s, 2H), 6.78 (s, 1H), 6.73 (s, 1H), 4.61 (t, 1H, J=7.32 Hz), 3.16-3.10 (m, 2H), 2.21 (s, 1H), 2.17 (s, 1H), 2.09-2.01 (m, 1H), 1.88-1.83 (m, 1H), 1.78-1.68 (m, 2H).

Example 1-4

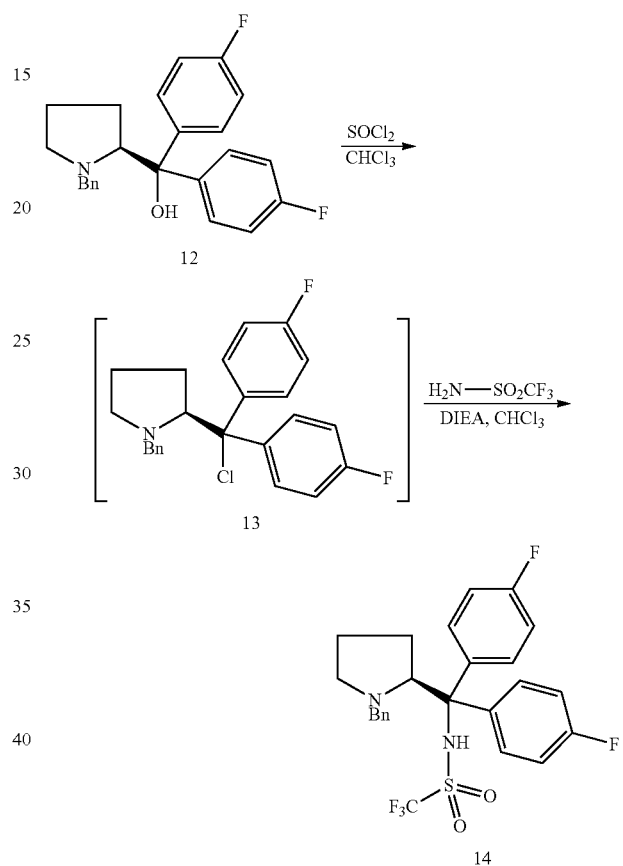

A mixture of a compound 12 (5.0 g, 13.2 mmol) and chloroform (10 mL) was ice-cooled, and then thionyl chloride (15.7 g, 132 mmol) was added dropwise to the mixture. The resultant mixture was stirred at room temperature for 15 hours, then toluene (40 mL) was added to the mixture, and then the solvent was distilled away under reduced pressure. A solution prepared by adding chloroform (40 mL) to the residue was added dropwise to a solution of diisopropylethylamine (8.5 g, 66 mmol) and trifluoromethanesulfonamide (2.2 g, 14.5 mmol) in chloroform (40 mL) at 0° C., and the resultant mixture was stirred at room temperature for 3 hours. A saturated aqueous ammonium chloride solution (80 mL) was added to the mixture, then the resultant mixture was extracted with ethyl acetate (3×40 mL), then an organic layer was dried over anhydrous sodium sulfate, and concentrated under reduced pressure. The residue was purified by silica gel column chromatography to produce a compound 14 as a brown solid material (1.57 g, 23%).

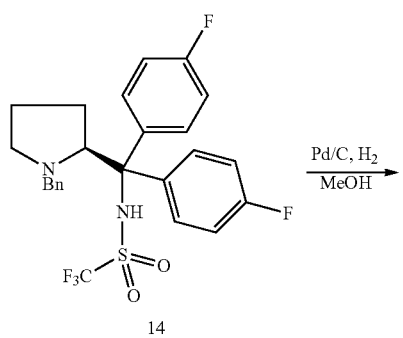

14

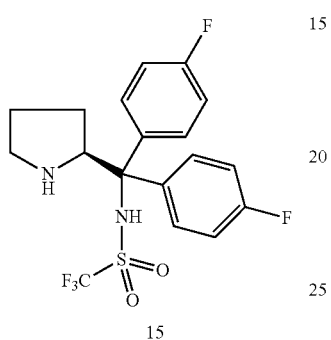

15

20% Pd(OH)₂/C (429 mg, Lot OH-2002, KAWAKEN) was added to a solution of a compound 14 (1.57 g, 3.0 mmol) in methanol (30 mL), and the resultant mixture was subjected to a hydrogenation reaction at 30° C. for 2 hours in an autoclave (0.5 MPa). The reaction mixture was filtrated, and a filtrate was concentrated under reduced pressure. The residue was purified by flash column chromatography to produce a compound 15 as a grayish white solid material (740 mg, 63%).

$^1$H NMR (CD$_3$OD, 400 MHz) δ 7.49-7.46 (m, 2H), 7.40-7.36 (m, 2H), 7.05-6.94 (m, 4H), 4.65 (t, 1H, J=7.8 Hz), 3.23-3.14 (m, 2H), 2.33-2.23 (m, 1H), 2.14-2.04 (m, 1H), 2.02-1.88 (m, 2H).

Examples 2

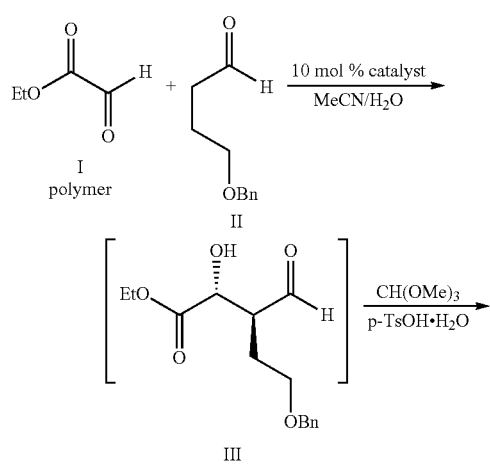

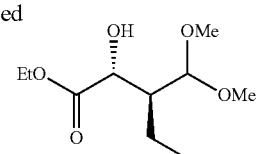

IV

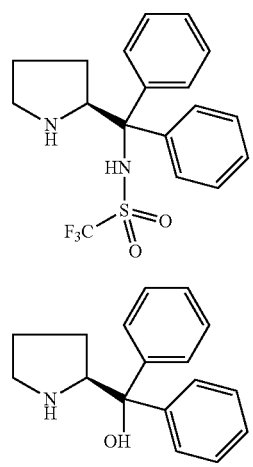

a b c

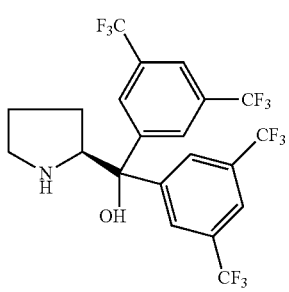

Water (108 µL, 6 mmol) and a solution of a polymer of compound (I) (602.9 mg, a 50.8% toluene solution, 3.0 mmol) were added to a solution of compound (II) (374.2 mg, 95.27%, 2.0 mmol) and a catalyst a, b, c, d or e (0.2 mmol each) in acetonitrile (2 mL) at 25° C. The resultant mixture was stirred at 25° C. for 20 hours, and then trimethyl orthoformate (1.06 g, 10 mmol) and p-toluenesulfonic acid monohydrate (38.0 mg, 0.2 mmol) were added sequentially to the mixture. After 2 hours, the diastereomer ratio (syn-IV/anti-IV) and the enantiomeric excess were measured. The solution was concentrated under reduced pressure, and then the residue was purified by flash column chromatography to produce a compound IV as a colorless oily material. The yield, the diastereomer ratio and the enantiomeric excess are shown in Table 1 below. The yield was a yield of the isolated compound IV and was determined as a yield of two steps.

The diastereomer ratio was measured by HPLC using reverse-phase column pack C$_{18}$MGIII (150×4.6 mm, 5 µm) under the following conditions.
Column temperature: about 30° C.
Mobile phase A: water/trifluoroacetic acid (1000/0.5)
Mobile phase B: acetonitrile/trifluoroacetic acid (1000/0.5)
Gradient Conditions:
0 (min); mobile phase A: 80%, mobile phase B: 20%
0 to 35 (min); mobile phase A: 80→50%, mobile phase B: 20→50%

35 to 50 (min); mobile phase A: 50→20%, mobile phase B: 50→80%
50 to 55 (min); mobile phase A: 20%, mobile phase B: 80%
55 to 55.5 (min); mobile phase A: 20→80%, mobile phase B: 80→20%
55.5 to 70 (min); mobile phase A: 80%, mobile phase B: 20%
Flow rate: 1.0 mL/min
UV detection: 215 nm
syn-IV, retention time: 31.2 min
anti-IV, retention time: 30.4 min The enantiomeric excess was measured by HPLC with arranging reverse-phase column CHIRALPAK AS-RH (4.6 mm×150 mm, 5 µm) and L-column ODS (4.6 mm×15 mm, 5 µm) tandemly under the following conditions.
Column temperature: about 30° C.
Mobile phase A: water
Mobile phase B: acetonitrile
Gradient Conditions:
0 (min); mobile phase A: 70%, mobile phase B: 30%
0 to 60 (min); mobile phase A: 70%, mobile phase B: 30%
60 to 60.1 (min); mobile phase A: 70→10%, mobile phase B: 30→90%
60.1 to 70 (min); mobile phase A: 10%, mobile phase B: 90%
70 to 70.1 (min); mobile phase A: 10→70%, mobile phase B: 90→30%
80 (min); mobile phase A: 70%, mobile phase B: 30%
Flow rate: 1.0 mL/min
UV detection: 220 nm
Minor enantiomer: 43.8 min
Major enantiomer: 45.8 min $^1$H NMR (CDCl$_3$, 400 Mz) δ 7.34-7.26 (m, 5H), 4.55 (d, 1H, J=12.0 Hz), 4.50 (d, 1H, J=12.0 Hz), 4.36 (d, 1H, J=7.3 Hz), 4.23 (q, 2H, J=7.3 Hz), 4.20-4.19 (m, 1H), 3.63-3.58 (m, 2H), 3.33 (s, 1H), 3.32 (s, 3H), 3.31 (s, 3H), 2.51-2.45 (m, 1H), 1.96-1.78 (m, 2H), 1.31 (t, 3H, J=7.1 Hz) [α]$^{25}_D$-17.2 (c 0.53, CH$_3$CN).

The same procedure was carried out in an NMP solvent using a catalyst d or e shown below in place of the catalyst a, b and c. The results are shown in Table 1.

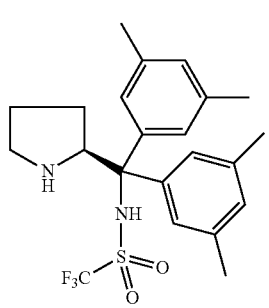

d

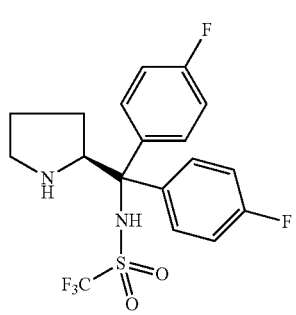

e

TABLE 1

| Catalyst | Yield (%) | anti:syn | ee (%) |
|---|---|---|---|
| a | 87 | 98:2 | 98 |
| b | 83 | 90:10 | 97 |
| c | 85 | 92:8 | 99 |
| d | 85 | 99:1 | >99 |
| e | 83 | 98:2 | >99 |

A catalyst represented by the following formula:

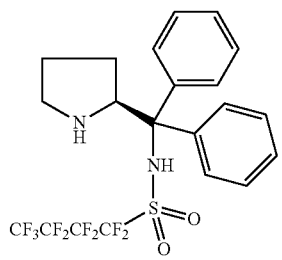

was used in place of the above-mentioned catalyst, and the reaction was carried out in an NMP solvent for 10 hours. As a result, the yield was 85% at anti:syn=99:1 and an ee value of 99% or more.

Examples 3

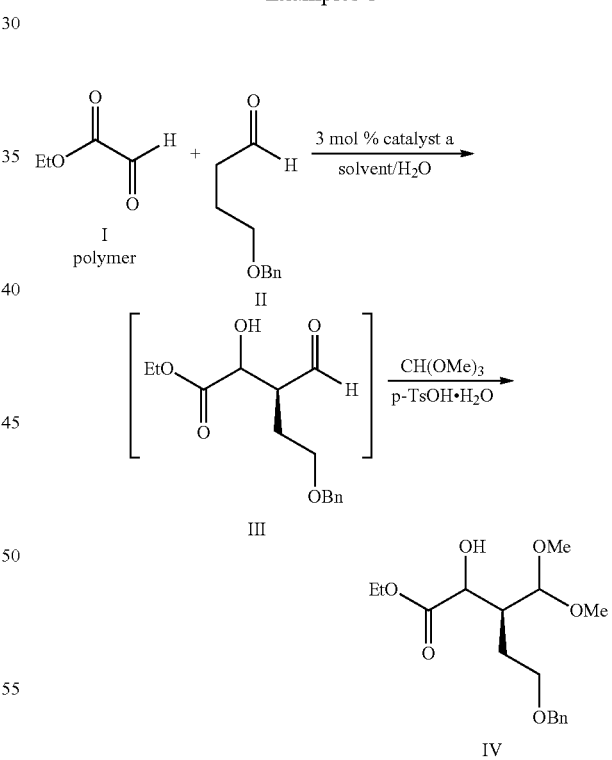

A compound II (1258.7 mg, a 70% toluene solution, 5.0 mmol) was added to a mixture of a solution of a polymer of compound (I) (1225.1 mg, a 50.8% toluene solution, 6.0 mmol), a catalyst a (78.5 mg, 0.15 mmol), water (270 µL) and a solvent shown in Table 2 (1.3 mL). The resultant mixture was stirred at room temperature (25-35° C.). After 20 hours, trimethyl orthoformate (10.6 g, 100 mmol) and p-toluenesulfonic acid monohydrate (47.6 mg, 0.25 mmol)

were added sequentially to the mixture, and the resultant mixture was stirred at room temperature for 3 hours. The solution was concentrated under reduced pressure, and then the residue was purified by flash column chromatography using heptane and ethyl acetate to produce a compound IV as a colorless oily material. The yield, the diastereomer ratio and the enantiomeric excess are shown in Table 2. The yield was a yield of the isolated compound IV and was determined as a yield of two steps. The diastereomer ratio and the enantiomeric excess are determined in the same manner as in Example 2.

TABLE 2

| Solvent | Yield (%) | anti:syn | ee (%) |
|---|---|---|---|
| THF | 95 | 94:6 | 95 |
| Toluene | 95 | 94:6 | 93 |

Examples 4

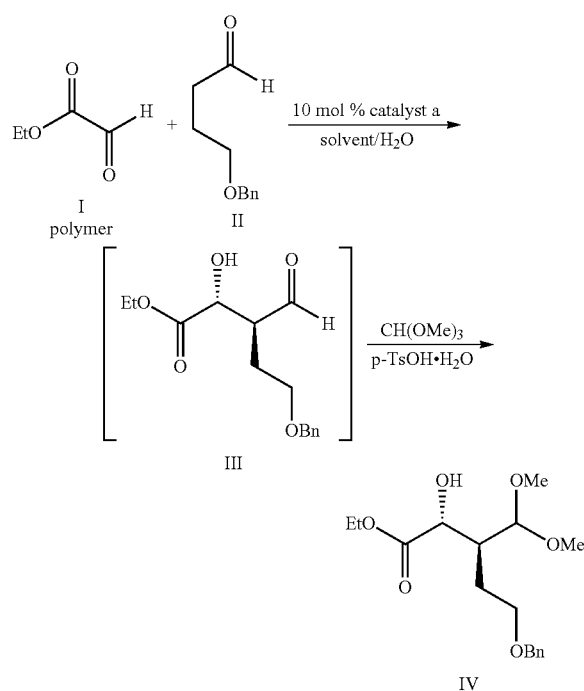

Water (54 μL, 3 mmol) and a solution of a polymer of compound (I) (301.4 mg, a 50.8% toluene solution, 1.5 mmol) were added to a mixture of a compound II (187.1 mg, 95.27%, 1.0 mmol), a catalyst a (38.4 mg, 0.1 mmol) and a solvent shown in Table 3 (1 mL) at 25° C., then the resultant mixture was stirred at a temperature shown in Table 3 for a period of time shown in Table 3, and then trimethyl orthoformate (1.06 g, 10 mmol) and p-toluenesulfonic acid monohydrate (19.0 mg, 0.1 mmol) were added sequentially to the mixture. After 2 hours, the diastereomer ratio (syn-IV/anti-IV) and the enantiomeric excess were determined in the same manner as in Example 2. Saturated sodium hydrogen carbonate (10 mL) was added to the reaction mixture, and the resultant mixture was extracted with MTBE (20 mL). An organic layer was washed with water (3×10 mL) and then dried over anhydrous magnesium sulfate, and concentrated under reduced pressure. The residue was purified by flash column chromatography to produce a compound IV. The yield, the diastereomer ratio and the enantiomeric excess are shown in Table 3. The yield was determined as a yield of two steps. Each of the yields of Examples 4-1 and 4-4 was a yield of the isolated compound IV, and the yield of each of other Examples was determined by adding biphenyl (154.2 mg, 1.0 mmol) as an internal reference to the reaction mixture and was measured by HPLC. The diastereomer ratio and the enantiomeric excess were determined in the same manner as in Example 2.

TABLE 3

| | Solvent | Temperature (° C.) | Time (h) | Yield (%) | anti:syn | ee (%) |
|---|---|---|---|---|---|---|
| Example 4-1 | CH$_3$CN | 25 | 20 | 87 | 98:2 | 98 |
| Example 4-2 | DMF | 25 | 20 | 78 | 98:2 | 99 |
| Example 4-3 | DMI | 25 | 20 | 88 | 99:1 | 99 |
| Example 4-4 | NMP | 25 | 20 | 83 | 99:1 | 99 |
| Example 4-5 | CH$_3$OH | 25 | 20 | 68 | 90:10 | 76 |
| Example 4-6 | Toluene | 25 | 20 | 75 | 95:5 | 97 |
| Example 4-7 | Chloroform | 25 | 20 | 79 | 94:6 | 96 |
| Example 4-8 | THF | 25 | 20 | 84 | 97:3 | 96 |
| Example 4-9 | EGDE | 25 | 20 | 83 | 98:2 | 98 |
| Example 4-10 | DMI | 0 | 40 | 84 | 99:1 | 99 |
| Example 4-11 | NMP | 0 | 40 | 82 | 99:1 | 99 |

Reference Example (Production Example of Compound (2))

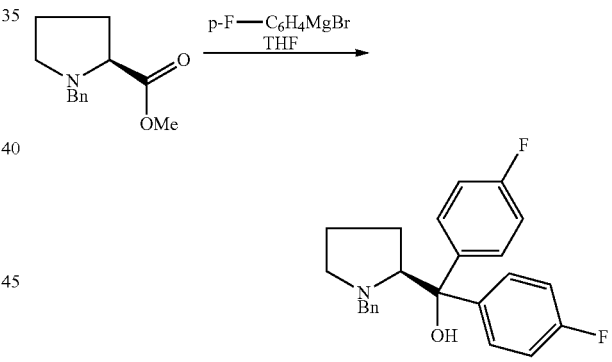

p-Fluorophenyl magnesium bromide (140 ml, 140 mmol) was added dropwise to a solution of N-benzylproline methyl ester (11 g, 50 mmol) in THF (150 ml), which was cooled to 0° C., and the resultant mixture was refluxed for three hours after the completion of the dropwise addition. The mixture was cooled to room temperature, then an aqueous ammonium chloride solution (75 ml) was added to the mixture, and then 1 N hydrochloric acid (75 ml) was further added to the mixture. The pH value of the mixture was adjusted to about 7.5 with a 2 N aqueous sodium hydroxide solution, and the mixture was extracted with ethyl acetate (3×150 mL). An organic layer was washed with brine (2×150 mL), the washed solution was dried over anhydrous magnesium sulfate, and concentrated under reduced pressure. A slurry prepared by adding ethyl acetate (10 mL) and heptane (200 mL) to the residue was refluxed for 1 hour. The resultant solution was air-cooled to produce a solid material, and the solid material was filtrated, was then washed with ethyl acetate/heptane (1/20, 150 mL) and then dried to produce a desired material as a yellow solid material (14.5 g, 75%).

INDUSTRIAL APPLICABILITY

The present invention provides compound (1) which can be used as a catalyst. When an aldol reaction is carried out in the presence of compound (1), a 3-formyl-2-hydroxypropanoic acid compound can be produced. Particularly when an optically active form of compound (1) is used, an optically active form of a 3-formyl-2-hydroxypropanoic acid compound can be produced with good selectivity.

The invention claimed is:

1. A compound represented by formula (1):

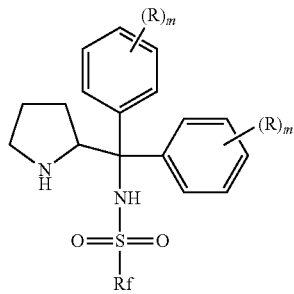
(1)

wherein Rf represents a $C_1$-$C_8$ perfluoroalkyl group; R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; and m represents an integer of 0 to 3.

2. The compound according to claim 1, wherein the compound represented by formula (1) is optically active.

3. A method for producing a compound represented by formula (1):

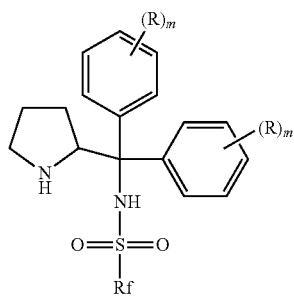
(1)

wherein Rf represents a $C_1$-$C_8$ perfluoroalkyl group; R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; and m represents an integer of 0 to 3; comprising the steps of:

introducing a leaving group into a compound represented by formula (2):

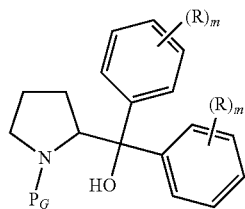
(2)

wherein R and m are as defined above; and $P_G$ represents a protecting group for an amino group to produce a compound represented by formula (3):

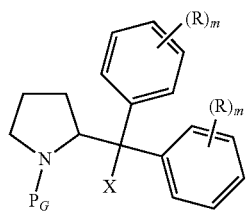
(3)

wherein X represents a leaving group; and R, m and $P_G$ are as defined above;

reacting compound (3) with ammonia to produce a compound represented by formula (4):

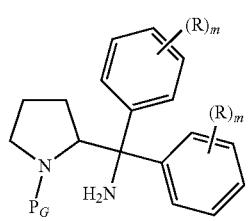
(4)

wherein $P_G$, R and m are as defined above or a salt thereof;

reacting compound (4) or a salt thereof with a $C_1$-$C_8$ perfluoroalkanesulfonylating agent to produce a compound represented by formula (5):

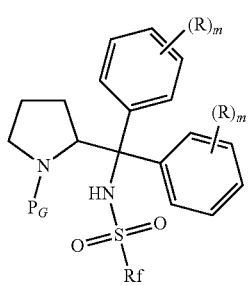
(5)

wherein Rf, $P_G$, R and m are as defined above; and deprotecting compound (5).

4. A method for producing a compound represented by formula (1):

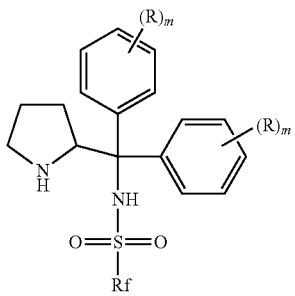

(1)

wherein Rf represents a $C_1$-$C_8$ perfluoroalkyl group; R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; and m represents an integer of 0 to 3; comprising the steps of:

introducing a leaving group into a compound represented by formula (2):

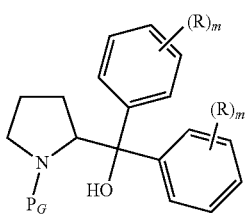

(2)

wherein Rf and m are as defined above; and $P_G$ represents a protecting group for an amino group to produce a compound represented by formula (3):

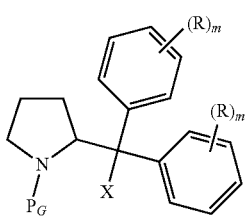

(3)

wherein X represents a leaving group; and R, m and $P_G$ are as defined above;

reacting the compound represented by formula (3) with trifluoromethanesulfonamide or a salt thereof to produce a compound represented by formula (5):

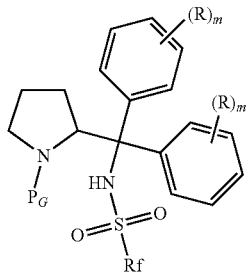

(5)

wherein Rf, $P_G$, R and m are as defined above; and deprotecting compound (5).

5. A method for producing a compound represented by formula (III):

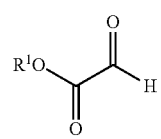

(III)

wherein $R^1$ represents a protecting group for a carboxyl group; and $R^2$ represents a protecting group for a hydroxyl group comprising the step of:

reacting a compound represented by formula (I):

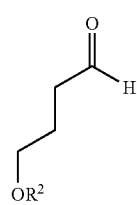

(I)

wherein $R^1$ is as defined above or a polymer thereof with a compound represented by formula (II):

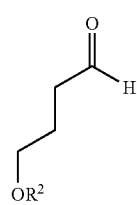

(II)

wherein $R^2$ is as defined above in the presence of a compound represented by formula (1):

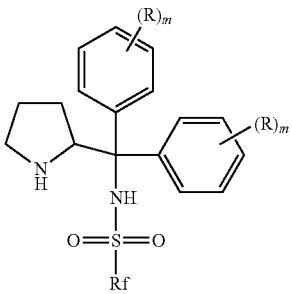
(1)

wherein Rf represents a $C_1$-$C_8$ perfluoroalkyl group; R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; and m represents an integer of 0 to 3.

6. The method according to claim 5, wherein the compound represented by formula (1) is an optically active form and an optically active form of the compound represented by formula (III) is produced.

7. A compound represented by formula (3a):

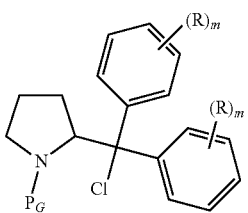
(3a)

wherein R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; m represents an integer of 0 to 3; and $P_G$ represents a protecting group for an amino group.

8. A compound represented by formula (5):

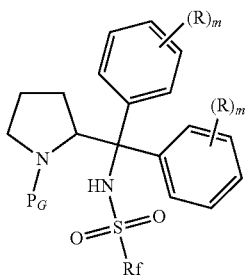
(5)

wherein R represents a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a nitro group, a cyano group or a halogen atom; m represents an integer of 0 to 3; $P_G$ represents a protecting group for an amino group; and Rf represents a $C_1$-$C_8$ perfluoroalkyl group.

* * * * *